(12) United States Patent
Camerlengo et al.

(10) Patent No.: US 12,163,562 B2
(45) Date of Patent: Dec. 10, 2024

(54) JOINT LOCKING MECHANISM

(71) Applicant: Precision Robotics Limited, London (GB)

(72) Inventors: Michele Camerlengo, London (GB); Jindong Liu, London (GB)

(73) Assignee: PRECISION ROBOTICS LIMITED, London (GB)

( * ) Notice: Subject to any disclaimer, the term of this patent is extended or adjusted under 35 U.S.C. 154(b) by 0 days.

(21) Appl. No.: 18/019,040

(22) PCT Filed: Sep. 29, 2022

(86) PCT No.: PCT/GB2022/052468
§ 371 (c)(1),
(2) Date: Jan. 31, 2023

(87) PCT Pub. No.: WO2023/057738
PCT Pub. Date: Apr. 13, 2023

(65) Prior Publication Data
US 2024/0255036 A1    Aug. 1, 2024

(30) Foreign Application Priority Data
Oct. 4, 2021 (GB) ..................... 2114193

(51) Int. Cl.
*F16D 63/00* (2006.01)
*B25J 9/10* (2006.01)
(Continued)

(52) U.S. Cl.
CPC ............ *F16D 63/006* (2013.01); *B25J 9/102* (2013.01); *B25J 17/00* (2013.01); *B25J 19/0004* (2013.01);
(Continued)

(58) Field of Classification Search
CPC ........ F16D 63/006; F16D 65/14; F16D 66/00; F16D 2066/003; F16D 2121/24;
(Continued)

(56) References Cited

U.S. PATENT DOCUMENTS 6,199,442 B1 * 3/2001 Bauer ..................... E02F 9/121
212/292
8,899,638 B2 * 12/2014 Flamm ..................... E05C 3/36
292/144
(Continued)

FOREIGN PATENT DOCUMENTS

CN   108381512 A  *  8/2018
DE   102011004370 A1 *  8/2012 ............. A61B 34/70
(Continued)

*Primary Examiner* — Adam D Rogers
(74) *Attorney, Agent, or Firm* — HSML P.C.

(57) ABSTRACT

A joint locking mechanism comprising a latch assembly and a gear movable relative to the latch assembly and comprising gear teeth. The latch assembly comprises an actuator moveable between a withdrawn position and a deployed position; first and second latches, each comprising an engagement element adapted to interlock with the gear teeth, each being moveable between an unlocked position and a locked position; a pivotable coupling comprising a first end coupled to the first latch, a second end coupled to the second latch, and a pivot positioned between the first and second ends which is rotatably coupled to the actuator. When the actuator is in the withdrawn position both the first and second latches are in the unlocked position. Movement of the actuator from the withdrawn position to the deployed position causes one, but not both, of the first and second latches to move to the locked position.

18 Claims, 9 Drawing Sheets

(51) Int. Cl.
*B25J 17/00* (2006.01)
*B25J 19/00* (2006.01)
*F16D 65/14* (2006.01)
*F16D 66/00* (2006.01)
*A61B 34/37* (2016.01)
*F16D 121/24* (2012.01)

(52) U.S. Cl.
CPC ............ *F16D 65/14* (2013.01); *F16D 66/00* (2013.01); *A61B 34/37* (2016.02); *F16D 2066/003* (2013.01); *F16D 2121/24* (2013.01)

(58) Field of Classification Search
CPC ........ B25J 9/102; B25J 17/00; B25J 19/0004; A61B 34/37
See application file for complete search history.

(56) References Cited

U.S. PATENT DOCUMENTS

| | | | | |
|---|---|---|---|---|
| 10,100,883 | B2 * | 10/2018 | Martin | F16D 23/00 |
| 10,441,441 | B2 * | 10/2019 | Kim | B25J 9/102 |
| 10,451,122 | B2 * | 10/2019 | Campton | F16D 41/14 |
| 11,015,666 | B2 * | 5/2021 | Bramson | F16D 63/006 |
| 11,858,481 | B2 * | 1/2024 | Kimes | B60T 17/22 |
| 2013/0264449 | A1 * | 10/2013 | Senelier | F16M 13/022 |
| | | | | 248/276.1 |
| 2016/0265608 | A1 * | 9/2016 | Corsetti | F16H 63/3433 |
| 2017/0254370 | A1 * | 9/2017 | Peglowski | F16D 41/12 |
| 2018/0058517 | A1 * | 3/2018 | Campton | F16D 41/084 |

FOREIGN PATENT DOCUMENTS

| | | | | |
|---|---|---|---|---|
| DE | 102021004499 A1 * | 3/2023 | | |
| EP | 2982482 A1 * | 2/2016 | | A61F 2/70 |
| KR | 20160069994 A * | 6/2016 | | |
| KR | 20170128713 A * | 11/2017 | | |
| WO | WO-2012077672 A1 * | 6/2012 | | A61B 90/50 |
| WO | WO-2017144302 A1 * | 8/2017 | | B25J 19/0004 |

* cited by examiner

JOINT LOCKING MECHANISM

CROSS-REFERENCE TO RELATED APPLICATIONS

This Application is a National Stage Application under 35 U.S.C. § 371 of PCT Application No. PCT/GB2022/052468, filed Sep. 29, 2022 which claims priority to UK Patent Application No. GB2114193.2, filed Oct. 4, 2021, the entire contents of which are incorporated by reference herein

BACKGROUND OF THE INVENTION

1. Field of the Invention

This invention relates to a joint locking mechanism for immobilising a movable joint within its range of motion, and more particularly although not exclusively, to a joint locking mechanism forming part of a master controller wherein the joint locking mechanism may lock a movable joint of the master controller.

2. Description of the Related Art

Known remote-control systems comprise a master controller, situated locally to an operator, and a slave device, situated remotely to the operator, wherein the system allows the slave device to be manipulated by the operator at a distance. Such systems may be useful if there is a barrier to direct manipulation. For example, a slave device may be used to carry out a minimally invasive surgical procedure in which direct manipulation of surgical tools by a surgeon is not possible due to restricted access to the patient's internal tissues and organs. Other examples may include military applications such as bomb disposal, emergency service applications such as search and rescue, and scientific research activities such as carrying out tasks in inhospitable environments (e.g. vacuums or high levels of reactivity) where direct manipulation could be hazardous or impossible.

For demonstrative purposes, the field of remote-control robotic surgical systems will be the focus from here on. However, this does not exclude the invention from being applied to other fields, such as those mentioned above.

In remote robotic surgery, a master controller is needed for transferring a surgeon's hand motion to a remote robotic instrument motion. Known master controllers comprise two manipulator arms for bimanual (two-handed) control that allows the control of a robotic instrument with each hand simultaneously.

The surgeon holds a handle at the end of each manipulator arm via fingers or the whole hand and moves the handle to control the robotic instruments while he or she monitors the robotic instruments via an endoscope image, for example. The manipulator arms can be classified into two categories: active and passive. An active manipulator arm has a motor to drive each joint and these motors allow the pose of the whole manipulator arm to be maintain regardless of whether the surgeon continues to hold the handle of the manipulator arm. This means that the surgeon can let go of the manipulator arm without risk of the manipulator arm dropping under the effect of gravity and a corresponding motion being replicated by the robotic instrument with the potential of harming a patient. Hence, the risk associated with dropping a manipulator arm handle is reduce and the surgeon may readily pause control of the robotic instrument to carry out a different task.

However, known active manipulator arms are bulky due to the complex components required to drive each joint at all times during use. The drive of the motors can also bias the motion of a surgeon's hand away from the intended motion, which can reduce the accuracy and precision achievable by the surgeon.

On the other hand, passive manipulator arms measure the position of each joint in the arm but do not actively drive each joint. This means that the manipulator arm will return to a 'floppy' state when surgeon's hand releases the handle and the manipulator arm will drop under the effect of gravity.

SUMMARY OF THE INVENTION

According to a first aspect of the invention there is provided a joint locking mechanism comprising a gear and a latch assembly, the gear being movable relative to the latch assembly and comprising a plurality of gear teeth, the latch assembly comprising:
  an actuator moveable between a withdrawn position and a deployed position;
  first and second latches, each comprising an engagement element adapted to interlock with the gear teeth, each being moveable between an unlocked position in which a respective latch is spaced apart from the gear, and a locked position in which a respective latch is in engagement with the gear such that the engagement element and gear teeth are interlocked;
  a pivotable coupling comprising a first end, a second end and a pivot positioned between the first and second ends, such that the first end is coupled to the first latch, the second end is coupled to the second latch, and the pivot is rotatably coupled to the actuator, wherein:
  when the actuator is in the withdrawn position both the first and second latches are in the unlocked position; and
  movement of the actuator from the withdrawn position to the deployed position causes one, but not both, of the first and second latches to move to the locked position.

In a passive manipulator arm, a movable joint forming part of the manipulator arm provides a degree of freedom, such as rotation about an axis or translation along an axis. For example, the manipulator arm may comprise a first limb coupled to a second limb via a movable joint. The latch assembly may be mounted to the first limb while the gear may be mounted to the second limb. The second limb could, for example, be rotatable relative to the first limb, in which case the gear would be a rotatable gear with a substantially circular cross-section. In another example, the second limb could translate telescopically with respect to the first limb, in which case the gear would be a linear gear similar to a rack of a rack and pinon mechanism.

By means of the invention, the movable joint (whether it is rotatable, telescopic or otherwise) may continue to be freely movable within the respective degree of freedom when the actuator is in the withdrawn position such that both the first and second latches are in the unlocked position and thus spaced apart from the gear.

However, if there is reason to lock the movable joint, the actuator may be moved to the deployed position such that one of the first and second latches is caused to move to the locked position and the engagement element of the respective latch is interlocked with the gear teeth. The movable joint may therefore be locked in any one of a plurality of configurations wherein each configuration is defined by an position of the gear with respect to the latch assembly. This could, for example, allow a surgeon to pause control of a surgical robot while attending to a separate task.

The first and second latches are each coupled to the actuator via the pivotable coupling which acts like a seesaw (or teeter-totter) wherein the actuator is the fulcrum about which the pivotable coupling pivots. When the actuator is in the deployed position, the pivotable coupling may pivot so that only one latch moves towards engagement with the gear.

If, for example, the gear is a rotatable gear (with a substantially circular cross-section) having 60 teeth, the resolution of the gear per latch is 6° (360°/60). This means that each latch may lock the gear in orientations 6° apart from one another. However, the first and second latches may be positioned relative to one another and the gear so that when the engagement element of one of the latches is interlocked with the gear teeth, the engagement element of the other latch abuts against an outermost edge of at least one gear tooth. The pivotable coupling allows either one of the first and second latches to be the latch that interlocks with the gear teeth while the other latch abuts against the outermost edge of at least one gear tooth.

As the first and second latches are engageable with the gear at different orientations, the resolution of the joint locking mechanism is double the resolution of the gear per latch. Therefore, in the example introduced above, the resolution of the joint locking mechanism would be 3° rather than 6°. In other words, one of the latches may engage with the gear every 3° of rotation. For example, the first latch could engage with the gear at 0°, 6°, 12°, etc. while the second latch could engage with the gear at 3°, 9°, 15°, etc.

It is to be understood that the same principle applies for a linear gear except that the resolution will be defined as a distance rather than an angle, the distance being dependent on the overall length of the linear gear and the number of teeth it comprises.

The finer the resolution of the joint locking mechanism, the more accurately the movable joint may be locked in the position it was last moved to prior to the actuator being deployed. However, typically, a finer resolution also means the teeth are smaller so the engagement that is possible between the latch and the gear is weaker.

By providing two latches, the resolution of the joint locking mechanism can be doubled (that is, made to be twice as fine) without needing to decrease the size of the gear teeth.

The pivotable coupling allows the two latches to engage with the gear independently of one another despite being actuated by the same actuator. Therefore, a single motor can be used to actuate the two latches which minimises the cost, weight and bulkiness associated with the joint locking mechanism.

Even though the provision of two latches doubles the resolution of the joint locking mechanism, it is still possible that that actuator could be moved to the deployed position when the gear is positioned such that neither engagement element is optimally positioned to interlock with the gear teeth. One solution to this is to provide sharp gear teeth and engagement elements so that it is not possible for both engagement elements to abut against an outermost edge of respective gear teeth. However, this would require intricate and expensive machining and the resulting engagement elements and gear teeth would be liable to wear quickly unless they were fabricated from hard materials that would further increase the associated machining costs.

In embodiments of the invention, the pivotable coupling may be resiliently deformable.

This allows the pivotable coupling to resiliently flex in a situation where the actuator is in the deployed position but both engagement elements are abutting against an outermost edge of respective gear teeth. In such a situation, both latches are biased towards the locked position and will continue to be so until the gear rotates slightly, relative to the latch assembly, in one direction or the other so that one latch can engage with the gear while the other latch becomes spaced apart from the gear due to the pivotable coupling pivoting about the actuator.

This avoids the need for the gear teeth and engagement elements to be sharp enough to avoid abutment of both engagement elements with respective gear teeth while also ensuring that there will be proper interlocking of one of the engagement elements with the gear teeth and, therefore, proper locking of the rotatable joint. As the gear teeth and corresponding engagement elements may be blunter than would otherwise be required, the pressure applied radially with respect to the gear is reduced and wear of the gear teeth and engagement elements is reduced accordingly. The resiliently deformable coupling therefore reduces wear of the gear teeth and engagement elements without sacrificing the force of engagement between the latch and the gear.

In embodiments of the invention, the engagement element may comprise a plurality of latch teeth. The latch teeth may be shaped similarly to the gear teeth so that they interlock with a close fit that maximises the surface areas that contact one another when the latch teeth and gear teeth are interlocking, thereby maximising the force required to overcome the lock.

In embodiments of the invention, the gear has a substantially circular cross-section and is rotatable about a joint axis. In such embodiments of the invention, the movable joint is a rotatable joint allowing a rotational degree of freedom through rotation about the joint axis.

In other embodiments, the gear is a linear gear movable perpendicularly to the joint axis in longitudinal directions. The movable joint is therefore a telescopic joint allowing a translational degree of freedom through translation of the rack relative to the joint axis.

In embodiments of the invention, the gear and the first and second latches are each shaped such that the gear teeth and the engagement elements are inclined relative to the joint axis such that the inclined engagement elements of each latch cooperate with the inclined gear teeth.

In such embodiments of the invention, a rotatable gear would be substantially conical or frustoconical where as a translatable linear gear could have a transverse cross-section which is, for example, trapezoidal or right-angled trapezoidal in shape.

The surfaces of the engagement element and the gear teeth which interlock with one another are inclined relative to the joint axis. This means that radial force (that is, force acting radially with respect to the joint axis) against the latch is partially deflected and converted into axial force (that is, force acting axially with respect to the joint axis), therefore reducing the force transferred to the pivotable coupling and reducing the likelihood of the pivotable coupling failing.

Also, the fact that the surfaces are inclined increases the size of the surface areas which contact against one another when the engagement element and gear teeth are interlocking without requiring an increase in the size of the gear and/or latches. Greater surface areas reduce the pressures applied between the latch and the gear and, in turn, reduce material deformation that might lead to weaker engagement of the latch and the gear.

In embodiments of the invention the latch assembly may further comprise a latch guide for supporting each latch and guiding each latch as it moves towards and away from the gear.

When one of the latches is engaged with the gear, the gear teeth may impart shear forces against the engagement element of the latch. The latch guide may be configured to support the latches to prevent them from being twisted out of position when shear forces are applied against them, for example.

The latch guide may also be configured to guide the latches so that they move directly from the unlocked position to the locked position and vice versa. This may be particularly beneficial when the pivotable coupling is resiliently deformable and the latches are being biased towards the locked position. If there was no latch guide to guide the latches, one or both of the latches might be caused to twist, due to the bias, before one of the engagement elements is able to fully interlock with the gear teeth.

In embodiments of the invention, each latch may be moveable relative to the latch guide substantially radially to the gear if the gear is rotatable (having a substantially circular cross-section), or substantially perpendicularly to the gear if the gear is translatable (linear).

In such embodiments of the invention, the forces which may be applied by the gear against one of the latches when it is in the locked position are predominantly in the tangential or longitudinal directions, respectively. Therefore, each latch is moveable substantially perpendicularly to the forces that may be applied against it, in use, by the gear. This reduces the likelihood that a force applied to one of the latches, by the gear, will cause movement of the latch from the locked position to the unlocked position. However, the gear teeth and engagement elements may be shaped so that some force applied by the gear against one of the latches when it is in the locked position is in the radial or transverse direction, respectively. The provision of a radial/transverse force (that is, a force in the direction in which the latch is moveable) may also be desirable as it may prevent the latch getting stuck in the locked position due to friction generated by the tangential/longitudinal force.

In embodiments of the invention, the actuator is moveable substantially perpendicularly to the joint axis.

In such embodiments of the invention, the actuator may be positioned substantially centrally between the first and second latches. Movement of the actuator substantially perpendicularly to the joint axis therefore moves each latch evenly towards the gear.

The fact that the actuator is moveable substantially perpendicularly to the joint axis may also minimise the distance it must move to cause the latches to move between the unlocked position and the locked position.

In embodiments of the invention, the pivotable coupling may be a first pivotable coupling; the latch assembly may comprise third and fourth latches each comprising an engagement element adapted to interlock with the gear teeth, each being moveable between an unlocked position in which a respective latch is spaced apart from the gear, and a locked position in which a respective latch is in engagement with the gear such that the engagement element and gear teeth are interlocked; the latch assembly may also comprise a second pivotable coupling comprising a first end, a second end and a pivot positioned between the first and second ends, such that the first end is coupled to the third latch, the second end is coupled to the fourth latch, and the pivot is rotatably coupled to the actuator; when the actuator is in the withdrawn position all latches may be in the unlocked position; and movement of the actuator from the withdrawn position to the deployed position causes one, but no others, of the first, second, third and fourth latches to move to the locked position.

In such embodiments of the invention, the resolution of the joint locking mechanism may be improved further by providing four latches rather than two. For example, if the gear is rotatable (substantially circular in cross-section) and has a resolution per latch of 6°, the overall joint locking mechanism may provide a resolution of just 1.5°. In other words, the angle between each orientation of the gear at which one of the four latches may engage with the gear would be just 1.5° despite each gear tooth occupying 6° of the gear.

The same principle applies if the gear is translatable (linear). A linear gear might have a resolution of 2 mm per latch, for example. Therefore, the provision of four latches would make the overall resolution of the joint locking mechanism four times as fine, i.e., 0.5 mm.

In embodiments of the invention, each pivotable coupling may be rotatably coupled to the actuator via an auxiliary coupling, the auxiliary coupling comprising a first end, a second end and a pivot positioned between the first and second ends, the first pivotable coupling is rotatably coupled to the first end of the auxiliary coupling, the second pivotable coupling is rotatably coupled to the second end of the auxiliary coupling, and the pivot is rotatably coupled to the actuator.

All four latches may, therefore, be moved between the unlocked and locked positions by a single actuator. This avoids the added bulkiness, weight and expense that would be associated with requiring more than one actuator to move the various latches.

In embodiments of the invention, the gear may comprise a first portion, with which the first and second latches are engageable, and a second portion, with which the third and fourth latches are engageable; the first portion may comprise a first plurality of gear teeth; and the second portion may comprise a second plurality of gear teeth off-set from the first plurality of gear teeth.

In such embodiments of the invention, the third and fourth latches may be configured identically to the first and second latches except that they are engageable with the second portion of the gear rather than the first portion. Also, the second portion of the gear may be off-set from the first portion so that when the gear is oriented about half way between two positions at which the first and second latches may engage with the gear respectively, one of the third and fourth latches may engage with the gear instead.

This avoids the need to space the four latches apart precisely enough that each latch is engageable with the same plurality of gear teeth as the gear rotates through very fine intervals of rotation, such as 1.5° for example.

It is to be understood that if the gear is a rotatable gear, the second plurality of gear teeth are tangentially off-set from the first plurality of gear teeth. Meanwhile, if the gear is a linear gear, the second plurality of gear teeth are longitudinally off-set from the first plurality of gear teeth.

In embodiments of the invention, the joint locking mechanism may further comprise a driving module for driving movement of the actuator between the withdrawn position and the deployed position. The driving module may comprise a motor or any other suitable linear driving component.

In embodiments of the invention, the joint locking mechanism may further comprise an actuator sensor adapted to sense when the actuator is in the withdrawn position or the deployed position.

In such embodiments of the invention, information sensed by the actuator sensor may be used to accurately stop a motor driving the actuator once the actuator has reached either the withdrawn position or the deployed position. This prevents the motor from under or over driving the actuator which could result in failed locking of the joint or too much force being applied to components such as the pivotable coupling as a result of the motor driving the actuator with too much force towards the gear. The actuator sensor therefore allows a motor driving the actuator to be controlled accurately and reliably.

The information sensed by the actuator sensor may also be used to indicate the position of the actuator to a user of the device comprising the rotatable joint. The user may thereby receive confirmation that his or her command to the actuator has been carried out and that the rotatable joint is either locked or freely rotatable.

In embodiments of the invention, the joint locking mechanism may further comprise a joint sensor adapted to measure the position of the gear relative to the latch assembly and hence the configuration of the movable joint. This information could be used to determine the pose of a manipulator arm comprising the movable joint, for example. Commands could then be sent to a slave robot based on the pose of the manipulator arm so that the slave robot follows the movements of the user.

If the gear is a rotatable gear, the joint sensor may sense the orientation of the circular gear relative to the latch assembly. If the gear is a linear gear, the joint sensor may sense the translational position of the linear gear relative to the latch assembly. Any suitable type of sensor could be used as the position sensor, such as a magnetic encoder or an optical encoder.

According to a second aspect of the invention there is provided a lockable joint assembly comprising a joint locking mechanism according to the first aspect of the invention, a first limb, and a second limb movably attachable to the first limb, wherein:
the latch assembly is mounted to the first limb;
the gear is mounted to the second limb; and
when one of the latches is engaged with the gear, the second limb is locked in position relative to the first limb.

If the gear is a rotatable gear, the first limb may comprise one of a rotor portion and a stator portion and the second limb may comprise the other of the rotor portion and the stator portion, wherein the rotor portion is engageable with the stator portion and is rotatable within the stator portion about the joint axis.

BRIEF DESCRIPTION OF THE DRAWINGS

The invention will now be described by way of example only with reference to the accompanying drawings in which.

DETAILED DESCRIPTION OF THE EMBODIMENTS

Figure 1:
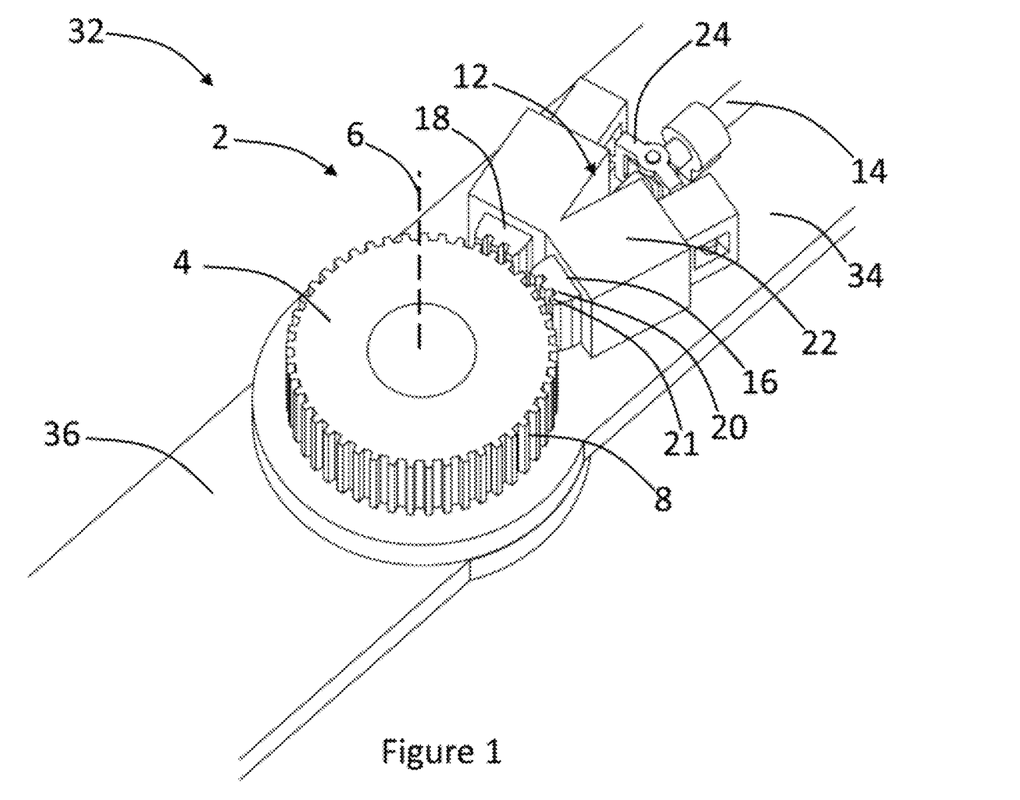
FIGS. 1, 2 and 3 show schematic representations of a lockable joint assembly according to an embodiment of the second aspect of the invention, wherein the actuator is in the withdrawn position.
Figure 2:
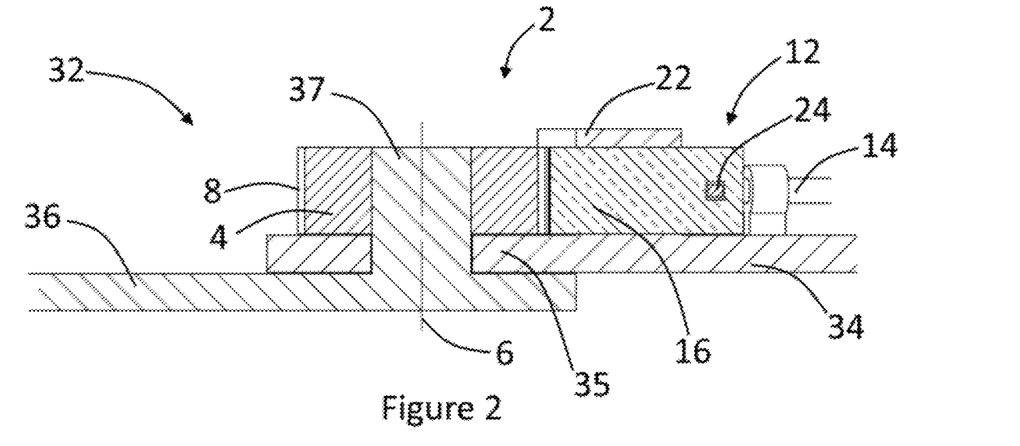
Figures 3, 4:
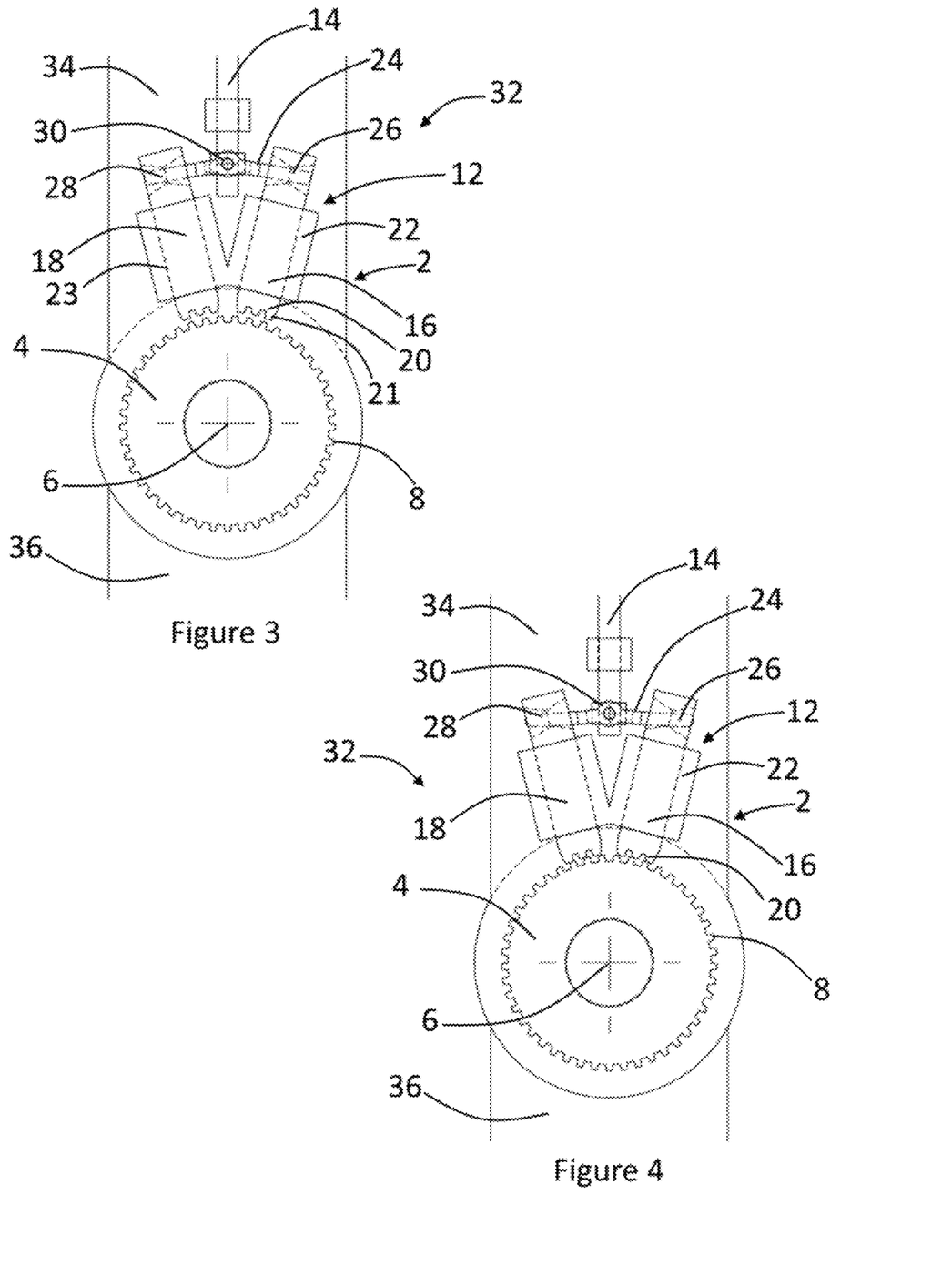
FIG. 4 shows a schematic representation of the lockable joint assembly shown in FIGS. 1 to 3, except the actuator is in the deployed position and the first and second latches are biased towards the locked position.

Referring initially to FIGS. 1, 2 and 3, a joint locking mechanism according to an embodiment of the invention is designated generally by the reference numeral 2. The joint locking mechanism 2 comprises a gear 4 (specifically a rotatable gear 4 having a substantially circular cross-section) which is rotatable about a joint axis 6 and comprises a plurality of gear teeth 8.

The joint locking mechanism 2 also comprises a latch assembly 12 comprising an actuator 14, a first latch 16, a second latch 18, a latch guide 22 and a pivotable coupling 24. The first and second latches 16, 18 each comprise an engagement element 20 adapted to interlock with the gear teeth 8. In this embodiment of the invention, each engagement element 20 comprises three latch teeth 21 which are shaped to fit between the gear teeth 8.

The latch guide 22 supports each latch 16, 18 and guides each latch 16, 18 as it moves towards and away from the gear 4. In particular, the latch guide 22 comprises a channel 23 (shown in FIG. 3) for each latch 16, 18 to move through, the channels extending substantially radially from the gear 4 so that each latch 16, 18 is moveable relative to the latch guide 22 substantially perpendicular to the joint axis 6.

Referring particularly to FIG. 3, the pivotable coupling 24 comprises a first end 26, a second end 28 and a pivot 30 positioned between the first and second ends 26, 28. The first end 26 is coupled to the first latch 16, the second end 28 is coupled to the second latch 18 and the pivot 30 is rotatably coupled to the actuator 14.

The actuator 14 is moveable substantially perpendicular to the joint axis 6 between a withdrawn position and a deployed position.

In FIGS. 1 to 3, the actuator 14 is in the withdrawn position and, due to the coupling of the first and second latches 16, 18 to the actuator 14 via the pivotable coupling 24, the first and second latches 16, 18 are both in an unlocked position in which the respective latch 16, 18 is spaced apart from the gear 4.

Referring now to FIG. 4, the actuator 14 is now in the deployed position having been moved from the withdrawn position shown in FIGS. 1 to 3. Movement of the actuator 14 towards the deployed position causes the first and second latches 16, 18 to move towards the gear 4. However, in FIG. 4, the gear 4 is orientated such that the engagement element 20 of each latch 16, 18 abuts against the outermost edges of respective gear teeth 8.

In this embodiment of the invention, the pivotable coupling 24 is resiliently deformable. This means that the pivotable coupling is able to flex in this situation where the actuator 14 is in the deployed position but neither latch 16, 18 can fully engage with the gear 4. As a result of the pivotable coupling 24 flexing, both latches 16, 18 are biased towards engaging with the gear 4.

Hence, when the joint locking mechanism 2 is in the configuration shown in FIG. 4, each latch 16, 18 will engage with the gear 4 following a slight rotation of the gear 4. However, the first and second latches 16, 18 are positioned relative to one another and to the gear 4 such that a maximum of one of the latches 16, 18 is able to engage with the gear when it is in a particular orientation with respect to the latch assembly. For example, if the gear is turned slightly in one direction, the first latch 16 may be able engage with the gear 4 (as shown in FIGS. 5 and 6) and if the gear 4 is turned slightly in the other direction, the second latch 18 may be able to engage with the gear 4 (as shown in FIGS. 7 and 8).

Figure 5:
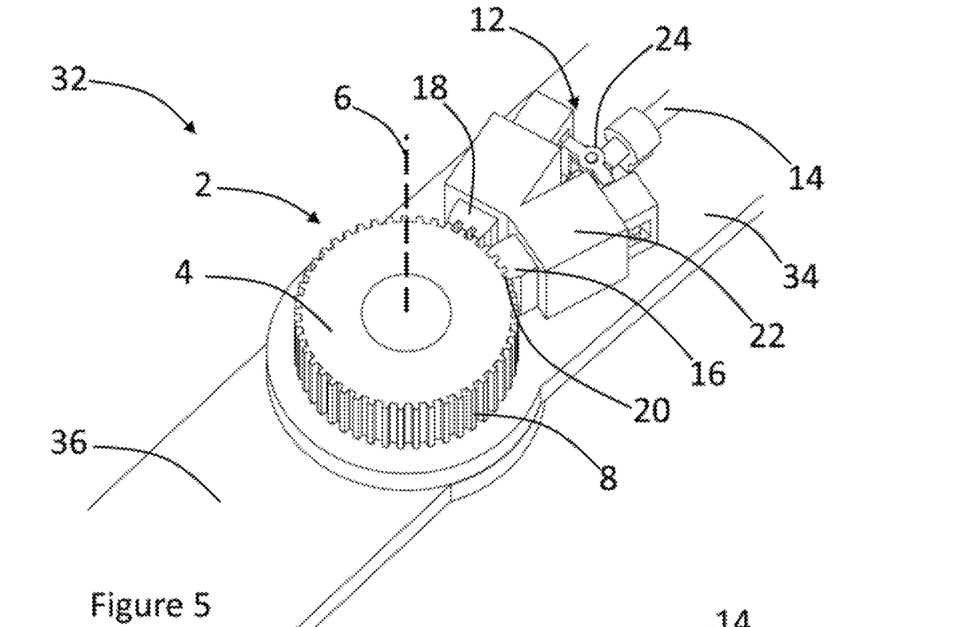
FIGS. 5 and 6 show the lockable joint assembly shown in FIGS. 1 to 3, except the actuator is in the deployed position and the first latch is in the locked position.
Figure 6:
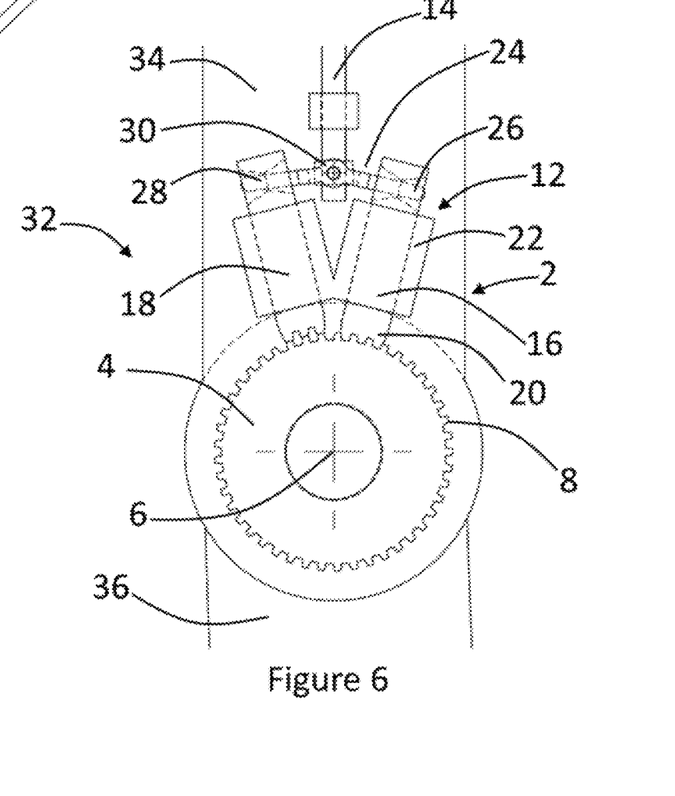

Referring now to FIGS. 5 and 6, the actuator 14 is in the deployed position and the gear 4 is orientated relative to the latch assembly such that the first latch 16 is in a locked position while the second latch 18 remains in an unlocked position due to the pivotable coupling 24 pivoting about the actuator 14. In the locked position, the first latch 16 is in engagement with the gear 4 such that the engagement element 20 is interlocked with the gear teeth 8.

Figure 7:
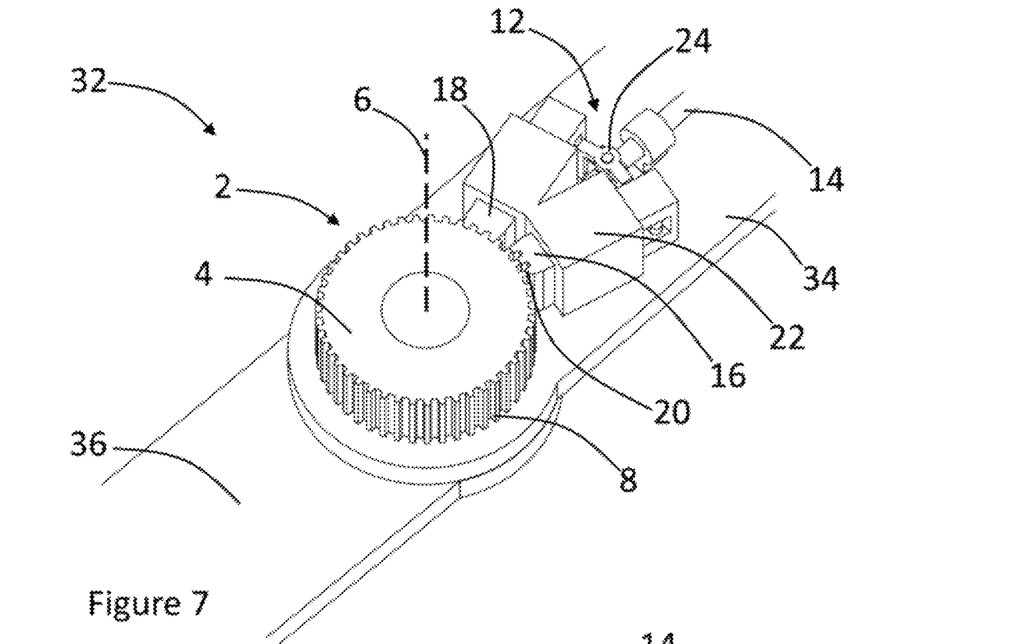
FIGS. 7 and 8 show the lockable joint assembly shown in FIGS. 1 to 3, except the actuator is in the deployed position and the second latch is in the locked position.
Figure 8:
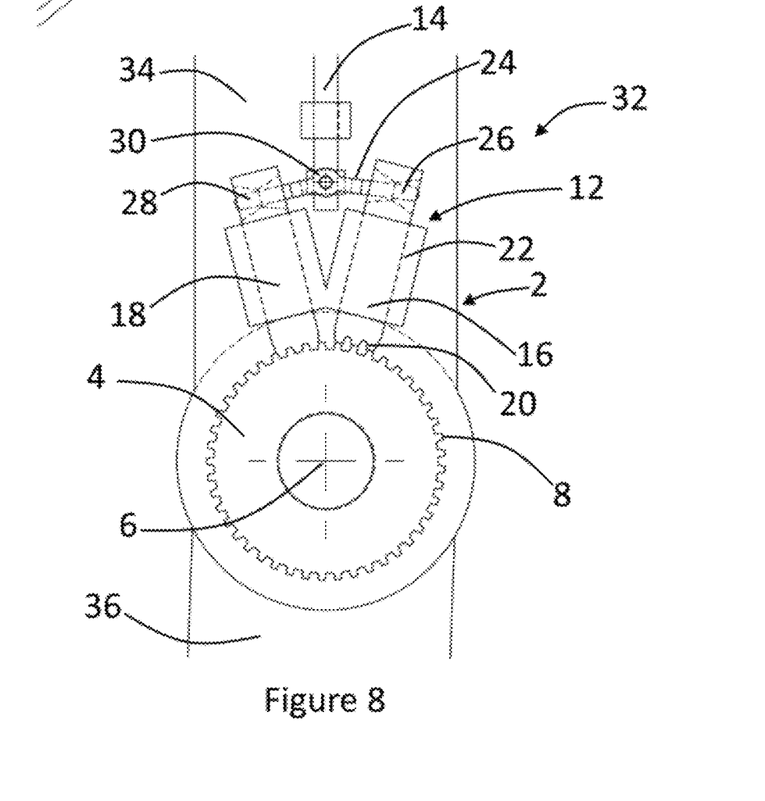

Similarly, in FIGS. 7 and 8, the actuator 14 is in the deployed position and the gear 4 is orientated such the second latch 18 is in a locked position in which it is in engagement with the gear 4 such that the engagement element 20 is interlocked with the gear teeth 8.

The pivotable coupling 24 allows each latch 16, 18 to be moved to the locked position independently of the other latch 16, 18 when the actuator 14 moves to the deployed position and therefore allows the pair of latches 16, 18 to be operated by a single actuator.

Referring now to all of FIGS. 1 to 8, the joint locking mechanism 2 forms part of a lockable joint assembly 32 that also comprises a first limb 34 and a second limb 36 rotatably attachable to the first limb 34.

The latch assembly 12 is mounted to the first limb 34 and the gear 4 is mounted to the second limb 36 so that the second limb is rotatable about the joint axis 6 with the gear 4 and relative to the latch assembly 12 and the first limb 34. When one of the latches 16, 18 is engaged with the gear 4, as shown in FIGS. 5 to 8, the second limb 36 is locked in position relative to the first limb 34.

Referring particularly to FIG. 2, the first limb 34 comprises a stator portion 35 and the second limb 36 comprises a rotor portion 37. The rotor portion 37 is engageable with the stator portion 35 and is rotatable within the stator portion 35 about the joint axis 6.

Figure 9:
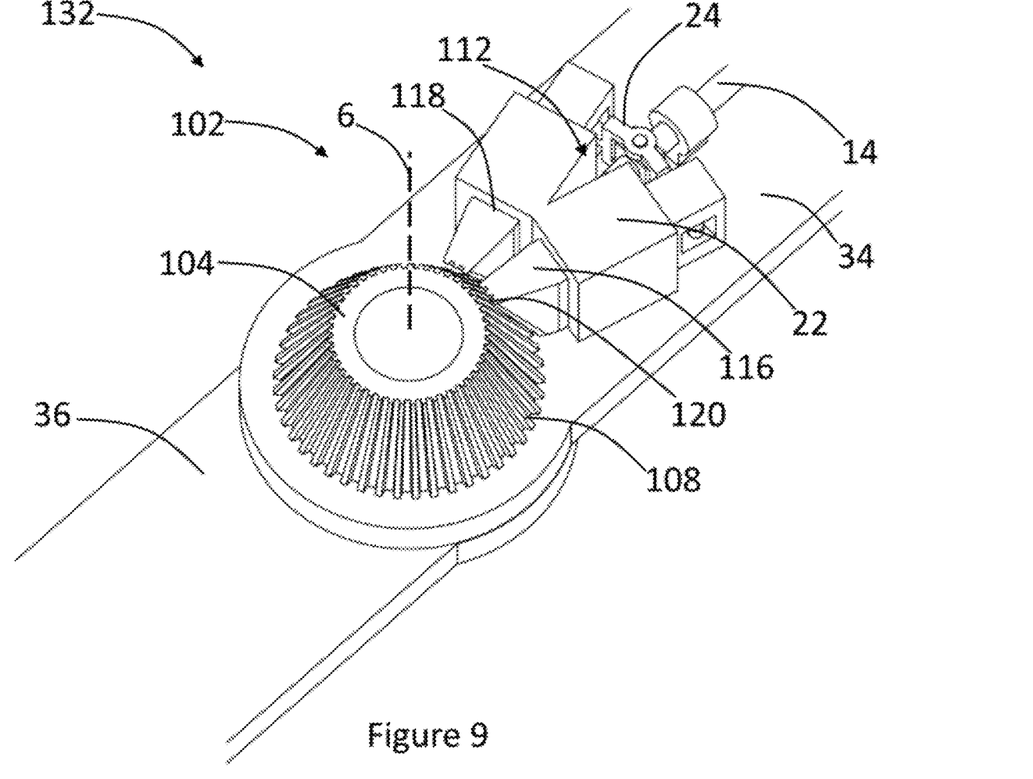
FIGS. 9 and 10 show schematic representations of a lockable joint assembly according to a different embodiment of the second aspect of the invention.
Figure 10:
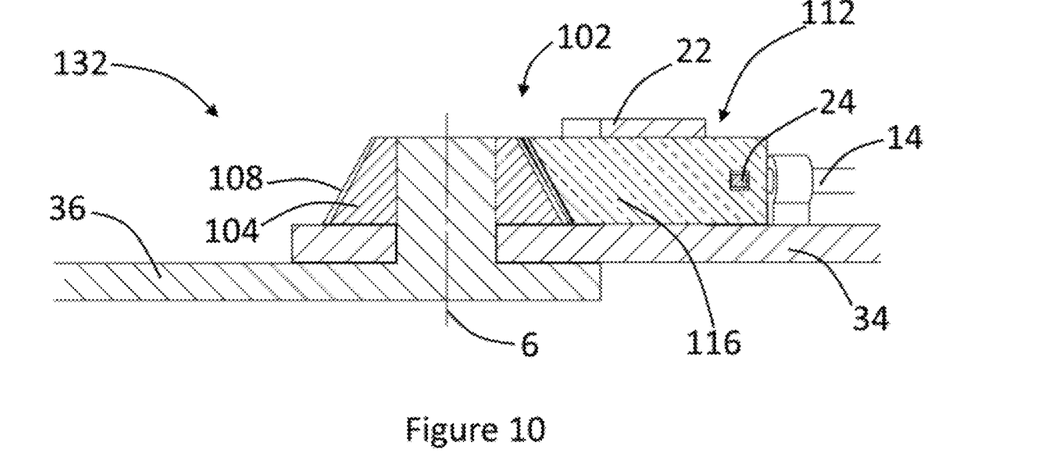

Referring now to FIGS. 9 and 10, a lockable joint assembly 132 is similar to the lockable joint assembly 32 shown in FIGS. 1 to 8 except that the gear 104 is substantially frustoconically shaped and the engagement element 120 of each latch 116, 118 is inclined relative to the joint axis 6 such that it cooperates with the frustoconical shape of the gear 104.

As a result of the gear teeth 108 and the engagement elements 120 being inclined with respect to the joint axis, the surface areas which contact one another when one of the engagement elements 120 interlocks with respective gear teeth 108 is increased without any of the components needing to increase in size. This therefore increases the force needed to overcome engagement of one of the latches 116, 118 with the gear 104.

Figure 11:
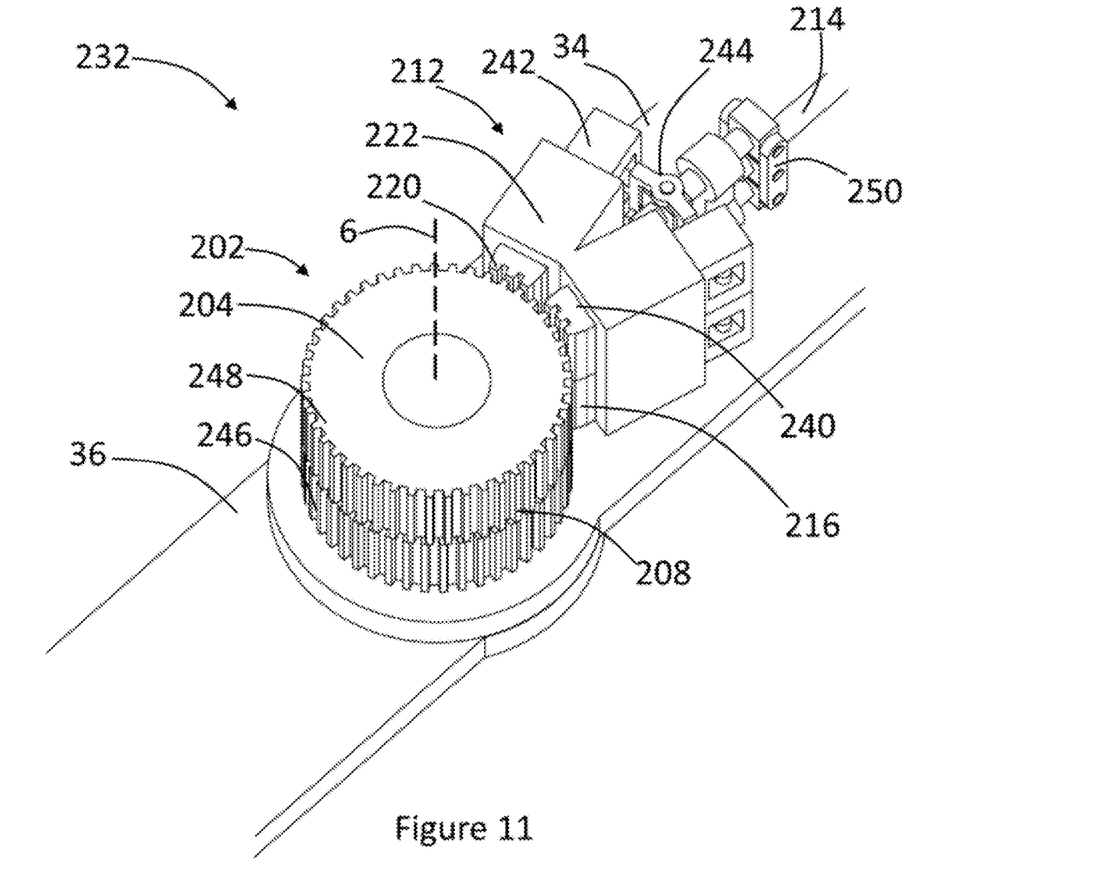
FIGS. 11, 12 and 13 show schematic representations of a lockable joint assembly according to another embodiment of the second aspect of the invention.
Figure 12:
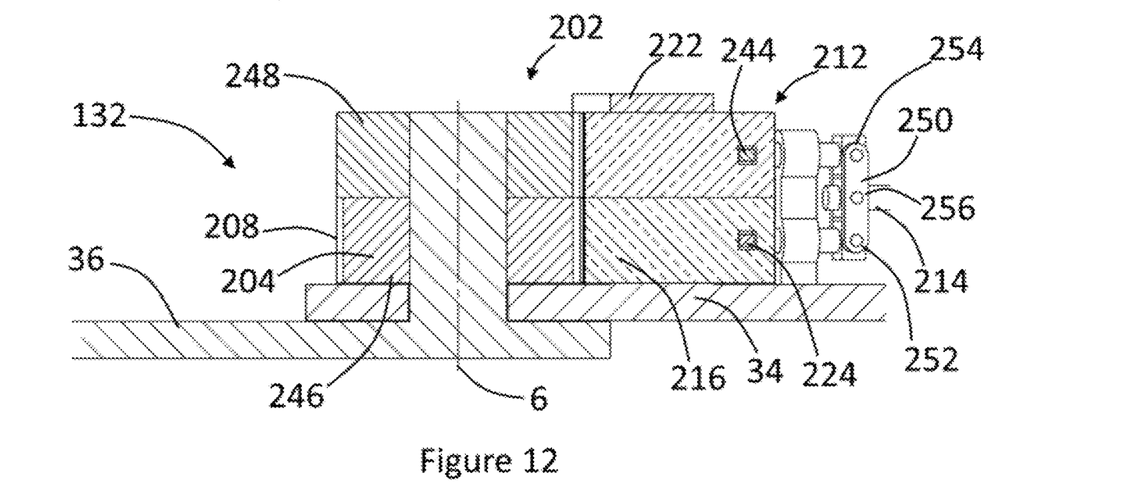
Figure 13:
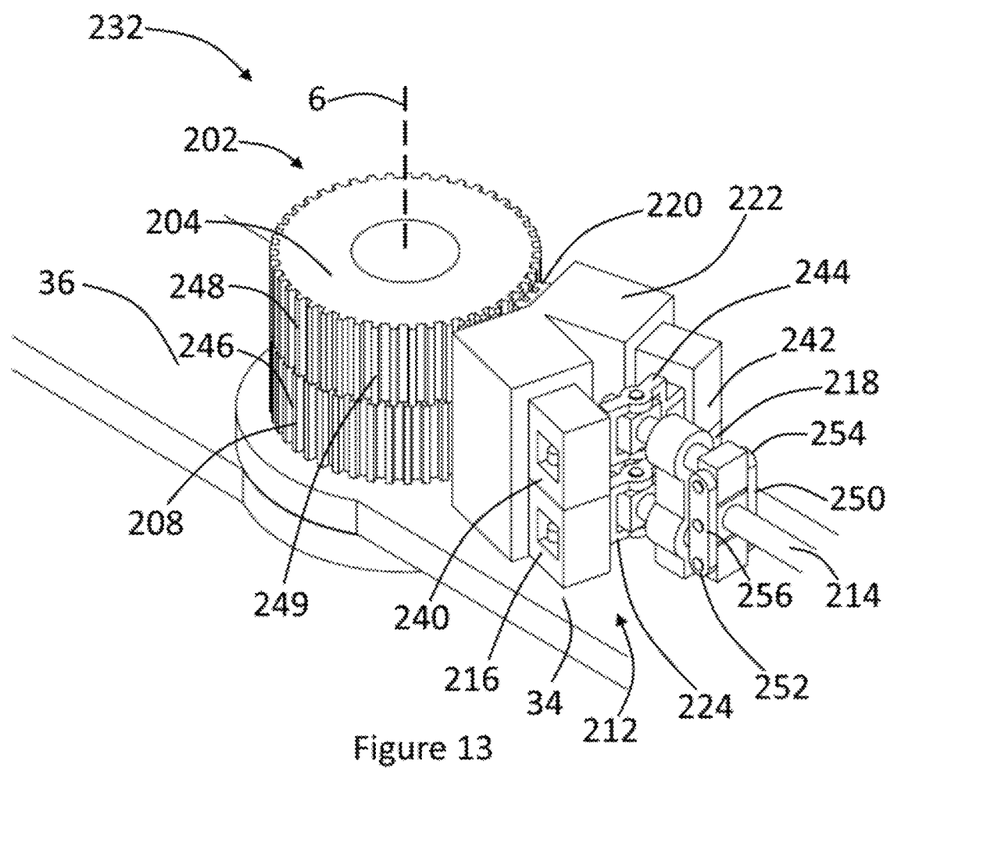

Referring now to FIGS. 11, 12 and 13, a lockable joint assembly 232 is similar to the lockable joint assembly 32 shown in FIGS. 1 to 8. However, the latch assembly 212 further comprises third and fourth latches 240, 242 each comprising an engagement element 220 adapted to interlock with the gear teeth 208, similarly to the first and second latches 216, 218. In this embodiment of the invention, the third and fourth latches 240, 242 are stacked above the first and second latches 216, 218 such that the first and third latches 216, 240 are moveable substantially parallel to one another and the second and fourth latches 218, 242 are also moveable substantially parallel to one another.

Also, in this embodiment of the invention, the pivotable coupling which couples the first and second latches 216, 218 to the actuator 214 is a first pivotable coupling 224 and the latch assembly 212 further comprises a second pivotable coupling 244 which is equivalent to the first pivotable coupling 224 except that it couples the third and fourth latches 240, 242 to the actuator 214.

The latch assembly 212 also comprises an auxiliary coupling 250. The auxiliary coupling comprises a first end 252, a second end 254 and a pivot 256 positioned between the first and second ends 252, 254. The first pivotable coupling 224 is rotatably coupled to the first end 252 of the auxiliary coupling 250 while the second pivotable coupling 244 is rotatably coupled to the second end 254 of the auxiliary coupling 250. The pivot 256 is rotatably coupled to the actuator 214, hence each pivotable coupling 224, 244 is rotatably coupled to the actuator 214 via an auxiliary coupling 250.

The gear 204 comprises a first portion 246 and a second portion 248. The first portion 246 comprises a first plurality of gear teeth 208, and the first and second latches 216, 218 are engageable with the first portion 246 such that the respective engagement element 220 interlocks with the first plurality of gear teeth 208. The second portion 248 comprises a second plurality of gear teeth 249 radially off-set from the first plurality of gear teeth 208. The third and fourth latches 240, 242 are engageable with the second portion 248 such that the respective engagement element 220 interlocks with the second plurality of gear teeth 249.

The radial offsetting of the second plurality of gear teeth 249 relative to the first plurality of gear teeth 208 means that the first and third latches 216, 240 are not engageable with the gear 204 at the same time as one another despite the first and third latches 216, 240 being moveable substantially along the same radial line relative to the gear 204. The same is true of the second and fourth latches 218, 242. Therefore, for a given orientation of the gear 204 only one of the first, second, third and fourth latches 216, 218, 240, 242 may be engageable with the gear 204.

When the actuator 214 is in the withdrawn position all latches 216, 218, 240, 242 are in the unlocked position. Then, when the actuator is in the deployed position, the combination of the first and second pivotable couplings 224, 244 and the auxiliary coupling 250 allows a single one the first, second, third and fourth latches 216, 218, 240, 242 to engage with the gear 204 such that the respective latch is in the locked position.

Figure 14:
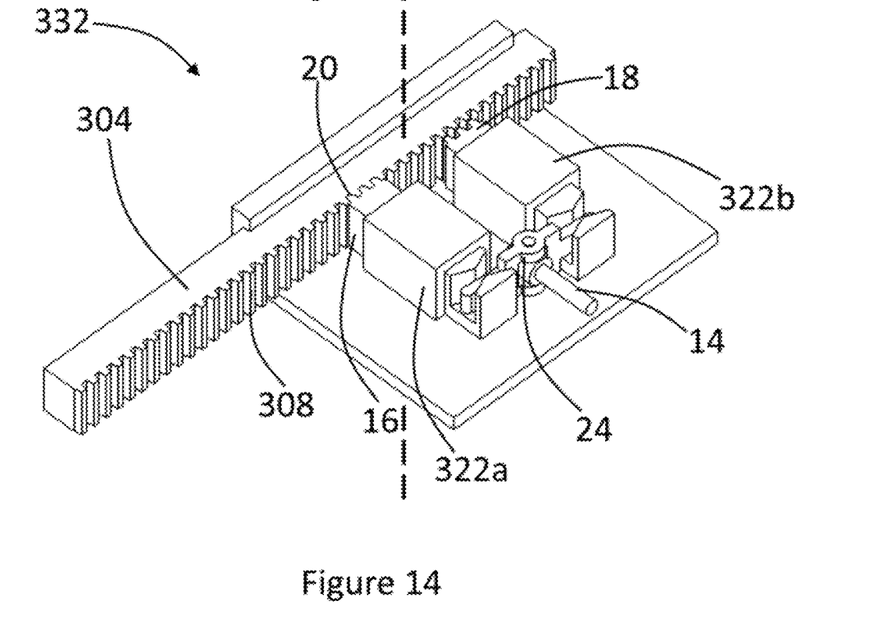
FIGS. 14 and 15 show schematic representations of a lockable joint assembly according to another embodiment of the second aspect of the invention.
Figure 15:
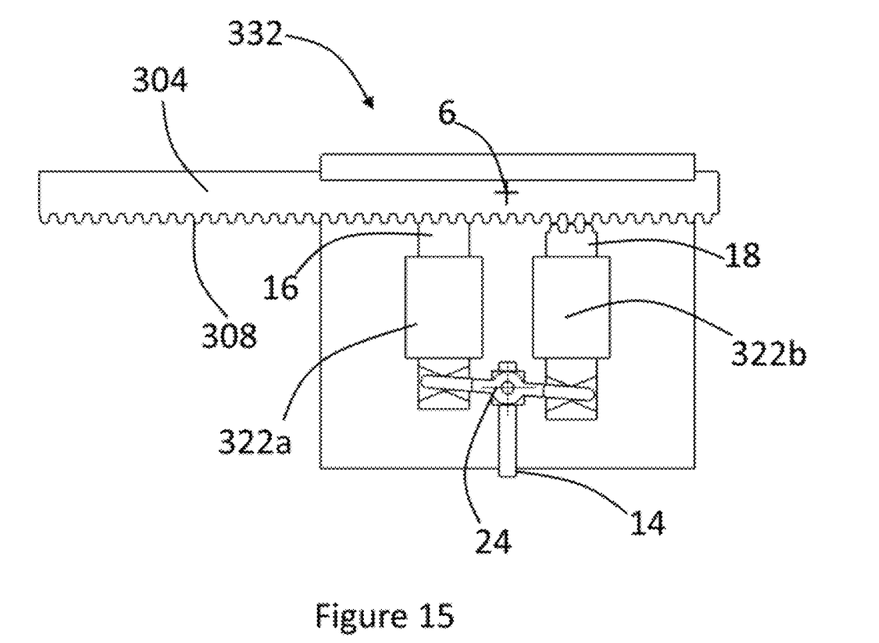

Referring now to FIGS. 14 and 15, a lockable joint assembly 332 comprises a joint locking mechanism 402 comprising a translatable linear gear 304 rather than a rotatable gear of the type exemplified in the preceding figures. The linear gear 304 is translational in longitudinal directions perpendicular to the joint axis 6 and comprises a plurality of gear teeth 308.

The joint locking mechanism 302 also comprises a latch assembly 312 similar to the latch assembly 12 shown in FIGS. 1 to 8 except that the latch guides 322a, 322b are positioned to guide the first and second latches 16, 18 so that they are movable perpendicularly to the movement of the linear gear 304. In other words the first and second latches 16, 18 are movable along axes which extend transversely relative to the linear gear 4 while the linear gear 304 is movable along an axis which extends longitudinally through the linear gear 304, a latch guide 22 and a pivotable coupling 24. The first and second latches 16, 18 each comprise an engagement element 20 adapted to interlock with the gear teeth 8.

Figure 16:
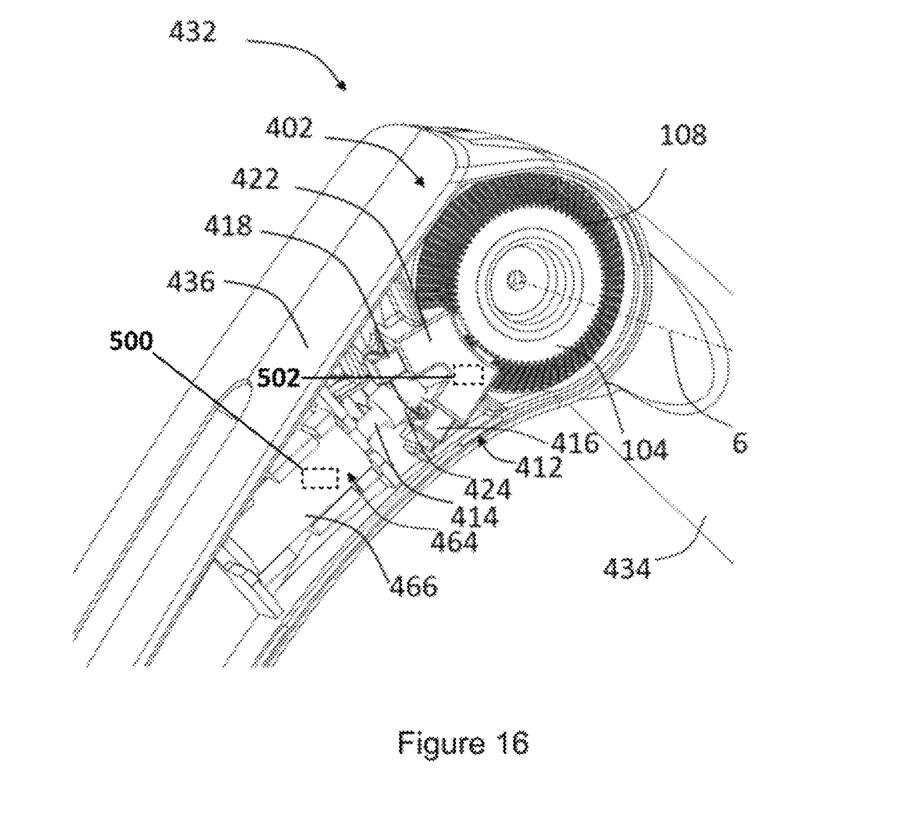
FIG. 16 shows a schematic representation of a lockable joint assembly according to a further embodiment of the second aspect of the invention.

Referring now to FIG. 16, a lockable joint assembly 432 is similar to the lockable joint assembly 132 shown in FIGS. 9 and 10 in that the gear 104 is substantially frustoconical.

In this embodiment of the invention, the joint locking mechanism 402 further comprises a driving module 464 for driving movement of the actuator 414 between the withdrawn position and the deployed position. The driving module 464 comprises a motor 466 configured to drive the linear movement of the actuator 414.

The lockable joint assembly 432, and particularly the first limb 434 and the second limb 436, form part of a manipulator arm which, in turn, forms part of a master controller (not shown) for controlling a slave robot (not shown.)

The joint locking mechanism 402 further comprises a position sensor associated with the actuator 414. The position sensor, acting as an actuator sensor 500, is adapted to sense whether the actuator is in the withdrawn position or the deployed position.

Based on information sensed by the position sensor, the motor 466 may be accurately controlled. In other words, the motor 466 may be reliably stopped once the actuator 414 has reached either the withdrawn position or the deployed position. This prevents the motor 466 from under or over driving the actuator 414 which could result in failed locking of the lockable joint assembly 432 or too much force being applied to components such as the pivotable coupling 424 as a result of the motor 466 driving the actuator with too much force towards the gear 104.

The information sensed by the position sensor may also be used to provide an indication to a user of the master controller of whether the rotatable joint is either locked or freely rotatable.

The joint locking mechanism 402 may further comprise a joint sensor 502 adapted to measure the position of the gear 104 relative to the latch assembly 412 and hence the configuration of the movable joint. This information could be used to determine the pose of a manipulator arm comprising the movable joint, for example. Commands could then be sent to a slave robot based on the pose of the manipulator arm so that the slave robot follows the movements of the user. If the gear 104 is a rotatable gear, the joint sensor 502 may sense the orientation of the circular gear relative to the latch assembly 412. If the gear 104 is a linear gear, the joint sensor 502 may sense the translational position of the linear gear 104 relative to the latch assembly 412.

The joint locking mechanism 402 also further comprises an angle sensor (not shown) adapted to measure the angle that the gear 104 is rotated about the joint axle 6 relative to the latch assembly 412.

The master controller may comprise a processor and the measured angle may be fed to the processor from the angle sensor. The measured angle may be processed to determine the pose of the manipulator arm comprising the rotatable joint and commands could then be sent to a slave robot based on the pose of the manipulator arm so that the slave robot follows the movements of the user.

Preferences and options for a given aspect, feature or parameter of the invention should, unless the context indicates otherwise, be regarded as having been disclosed in combination with any and all preferences and options for all other aspects, features and parameters of the invention. For example, a linear gear similar to the linear gear 304 shown in FIGS. 14 and 15 should be regarded as having been disclosed in combination with a latch assembly having third and fourth latches, such as the latch assembly 212 shown in FIGS. 11, 12 and 13.

The invention claimed is:

1. A joint locking mechanism comprising a gear and a latch assembly, the gear being movable relative to the latch assembly and comprising a plurality of gear teeth, the latch assembly comprising:
    an actuator moveable between a withdrawn position and a deployed position;
    first and second latches, each comprising an engagement element adapted to interlock with the gear teeth, each being moveable between an unlocked position in which a respective latch is spaced apart from the gear, and a locked position in which a respective latch is in engagement with the gear such that the engagement element and gear teeth are interlocked;
    a pivotable coupling comprising a first end, a second end and a pivot positioned between the first and second ends, such that the first end is coupled to the first latch, the second end is coupled to the second latch, and the pivot is rotatably coupled to the actuator, wherein:
    when the actuator is in the withdrawn position both the first and second latches are in the unlocked position; and
    movement of the actuator from the withdrawn position to the deployed position causes one, but not both, of the first and second latches to move to the locked position, wherein each engagement element comprises a plurality of latch teeth.

2. A joint locking mechanism according to claim 1, wherein the pivotable coupling is resiliently deformable.

3. A joint locking mechanism according to claim 1, wherein the gear has a substantially circular cross-section and is rotatable about a joint axis.

4. A joint locking mechanism according to claim 3, wherein the gear and the first and second latches are each shaped such that the gear teeth and the engagement elements are inclined relative to the joint axis and such that the inclined engagement elements of each latch cooperate with the inclined gear teeth.

5. A joint locking mechanism according to claim 3, wherein the latch assembly further comprises a latch guide for supporting each latch and guiding each latch as it moves towards and away from the gear.

6. A joint locking mechanism according to claim 5, wherein each latch is moveable relative to the latch guide substantially radially to the gear.

7. A joint locking mechanism according to claim 3, wherein the actuator is moveable substantially perpendicularly to the joint axis.

8. A joint locking mechanism according to claim 1, wherein:
    the pivotable coupling is a first pivotable coupling;
    the latch assembly further comprises third and fourth latches each comprising an engagement element adapted to interlock with the gear teeth, each being moveable between an unlocked position in which a respective latch is spaced apart from the gear, and a locked position in which a respective latch is in engagement with the gear such that the engagement element and gear teeth are interlocked;

the latch assembly also further comprises a second pivotable coupling comprising a first end, a second end and a pivot positioned between the first and second ends, such that the first end is coupled to the third latch, the second end is coupled to the fourth latch, and the pivot is rotatably coupled to the actuator;

when the actuator is in the withdrawn position all latches are in the unlocked position; and movement of the actuator from the withdrawn position to the deployed position causes one, but no others, of the first, second, third and fourth latches to move to the locked position.

9. A joint locking mechanism according to claim 8, wherein each pivotable coupling is rotatably coupled to the actuator via an auxiliary coupling, the auxiliary coupling comprising a first end, a second end and a pivot positioned between the first and second ends, the first pivotable coupling is rotatably coupled to the first end of the auxiliary coupling, the second pivotable coupling is rotatably coupled to the second end of the auxiliary coupling, and the pivot is rotatably coupled to the actuator.

10. A joint locking mechanism according to claim 8, wherein:

the gear comprises a first portion, with which the first and second latches are engageable, and a second portion, with which the third and fourth latches are engageable;

the first portion comprises a first plurality of gear teeth; and the second portion comprises a second plurality of gear teeth off-set from the first plurality of gear teeth.

11. A joint locking mechanism according to claim 1, further comprising a driving module for driving movement of the actuator between the withdrawn position and the deployed position.

12. A joint locking mechanism according to claim 11, wherein the driving module comprises a motor.

13. A joint locking mechanism according to claim 1, further comprising an actuator sensor adapted to sense when the actuator is in the withdrawn position or the deployed position.

14. A joint locking mechanism according to claim 1, further comprising a joint sensor adapted to measure the position of the gear relative to the latch assembly.

15. A lockable joint assembly comprising a joint locking mechanism according to claim 1, a first limb, and a second limb movably attachable to the first limb, wherein:

the latch assembly is mounted to the first limb;

the gear is mounted to the second limb; and when one of the latches is engaged with the gear, the second limb is locked in position relative to the first limb.

16. A joint locking mechanism according to claim 1, wherein the gear is a linear gear translatable in longitudinal directions.

17. A joint locking mechanism according to claim 16, wherein the latch assembly further comprises a latch guide for supporting each latch and guiding each latch as it moves towards and away from the gear.

18. A joint locking mechanism according to claim 17, where each latch is movable relative to the latch guide substantially perpendicularly to the gear.

* * * * *